(12) United States Patent
Yanai et al.

(10) Patent No.: US 10,400,273 B2
(45) Date of Patent: Sep. 3, 2019

(54) SYSTEM AND METHOD FOR SINGLE CELL GENETIC ANALYSIS

(71) Applicant: Technion Research & Development Foundation Limited, Haifa (IL)

(72) Inventors: Itai Yanai, Zichron Yaakov (IL); Uri Sivan, Haifa (IL); Elad Brod, Haifa (IL); Tamar Hashimshony, Haifa (IL); Anatoly Senderovich, Tiberias (IL)

(73) Assignee: Technion Research & Development Foundation Limited, Technion, Haifa (IL)

( * ) Notice: Subject to any disclaimer, the term of this patent is extended or adjusted under 35 U.S.C. 154(b) by 29 days.

(21) Appl. No.: 15/548,653

(22) PCT Filed: Feb. 4, 2016

(86) PCT No.: PCT/IB2016/050589
§ 371 (c)(1),
(2) Date: Aug. 3, 2017

(87) PCT Pub. No.: WO2016/125106
PCT Pub. Date: Aug. 11, 2016

(65) Prior Publication Data
US 2018/0023128 A1      Jan. 25, 2018

(30) Foreign Application Priority Data
Feb. 5, 2015   (GB) .................................. 1501907.8

(51) Int. Cl.
| | | |
|---|---|---|
| *C12Q 1/6837* | (2018.01) | |
| *B01L 3/00* | (2006.01) | |
| *G01N 33/487* | (2006.01) | |
| *C12Q 1/6874* | (2018.01) | |

(52) U.S. Cl.
CPC ........ *C12Q 1/6837* (2013.01); *B01L 3/50273* (2013.01); *B01L 3/50851* (2013.01); *B01L 3/502761* (2013.01); *C12Q 1/6874* (2013.01); *G01N 33/48721* (2013.01); *B01L 2200/028* (2013.01); *B01L 2300/0636* (2013.01); *B01L 2300/0819* (2013.01); *B01L 2300/0851* (2013.01)

(58) Field of Classification Search
CPC .......................... C12Q 1/6837; B01L 3/50273
See application file for complete search history.

(56) References Cited

U.S. PATENT DOCUMENTS

| | | | |
|---|---|---|---|
| 9,862,993 B2 * | 1/2018 | Tanabe ................. | C12Q 1/6809 |
| 10,030,240 B2 * | 7/2018 | Shirai ................ | C12N 15/1003 |
| 2010/0047790 A1 * | 2/2010 | Southern ............... | B01L 3/0293 |
| | | | 435/6.11 |
| 2011/0111981 A1 | 5/2011 | Love et al. | |
| 2014/0066318 A1 | 3/2014 | Frisen et al. | |
| 2015/0299784 A1 * | 10/2015 | Fan ...................... | C12Q 1/6874 |
| | | | 506/4 |

FOREIGN PATENT DOCUMENTS

| | | | |
|---|---|---|---|
| JP | WO 2014/141386 | * | 9/2014 |
| WO | 2007/022026 A2 | | 2/2007 |
| WO | 2010/142954 A1 | | 12/2010 |
| WO | 2012/048341 A1 | | 4/2012 |
| WO | 2012/162779 A1 | | 12/2012 |
| WO | 2013/180567 A2 | | 12/2013 |
| WO | 2013/188872 A1 | | 12/2013 |
| WO | 2014/108850 A2 | | 7/2014 |
| WO | 2014/137193 A1 | | 9/2014 |
| WO | 2014/201273 A1 | | 12/2014 |
| WO | 2015/118551 A1 | | 8/2015 |

OTHER PUBLICATIONS

Stähl et al., "Visualization and analysis of gene expression in tissue sections by spatial transcriptomics", Science, vol. 353, Issue 6294, pp. 78-82, (2016).
Hashimshony et al., "CEL-Seq: Single-Cell RNA-Seq by Multiplexed Linear Amplification", Cell Reports, vol. 2, pp. 666-673, (2012).
Chen et al., "An automated microfluidic device for assessment of mammalian cell genetic stability", Lab Chip., (2012), vol. 12, No. 20, pp. 3930-3935.

\* cited by examiner

*Primary Examiner* — Narayan K Bhat
(74) *Attorney, Agent, or Firm* — Vorys, Sater, Seymour and Pease LLP

(57) ABSTRACT

Provided are methods and systems for parallel analysis of a single cell's nucleic acid.

17 Claims, 3 Drawing Sheets

SYSTEM AND METHOD FOR SINGLE CELL GENETIC ANALYSIS

FIELD OF INVENTION

The present invention is directed to kits and methods for molecular diagnostics. Specifically, but not exclusively, the invention concerns methods and systems useful for genetic analysis of single cells.

BACKGROUND OF THE INVENTION

In many biomedical applications it is important to characterize the population of RNAs in a cell. This is useful in many research applications and clinical diagnostics. Certain quantitative genetic analyses of biological tissues and organisms are best performed at the single cell level. However, single cells only contain picograms of genetic material. Molecular protocols have been introduced to reveal the transcriptome by sequencing the RNAs of individual cells.

Microscopy, fluorescence-activated cell sorting (FACS), or real-time PCR-based methods can provide a single-cell aspect to experiments but are able to assay only a handful of genes at a time. High-throughput technologies such as microarrays and RNA-Seq provide a full view of the expression of all genes, but require more genetic material than is found in a single cell and are usually performed with thousands to millions of cells. These techniques provide useful genetic information at the cell population level, but have serious limitations for understanding biology at the single cell level.

Recently, a method, referred to as CEL-Seq protocol, was developed for overcoming the limitation of the small starting amount of RNA (Hashimshony et al., 2012, Cell Reports 2, p 666-673). The method utilizes barcoding and pooling samples before linearly amplifying mRNA with the use of one round of in vitro transcription. The described method showed more reproducible, linear, and sensitive results than a PCR-based amplification method. The robust transcriptome quantifications enabled by the method was also demonstrated to be useful for transcriptomic analyses of complex tissues containing populations of diverse cell types.

In order to identify transcriptomes, several methods that scale up have been introduced. Current biological tools also lack the capacity to assay genetic measurements in many single cells in parallel. Conventional single cell techniques are slow, tedious, and limited in the quantity of cells that can be analyzed at once. Microfluidics has been used to automate the process, achieving on the order of 100 cells per run, each very expensive. Robotics has also been developed to scale up the process to an order of magnitude of 1000 cells. However, both approaches involve the purchase of costly machines and parts, and in both of them the process is time consuming and not straight forward.

U.S. patent application No. 2014/0066318 describes methods and products for the localized or spatial detection of nucleic acid in a tissue sample. International patent applications Nos. WO 2013/180567, WO 2007/022026, WO 2010/142954, WO 2013/188872, WO 2014/201273 and U.S. patent application US 2011/0111981 relate to single cell isolation and/or analysis.

International patent applications No. WO 2015/118551 provides provided an apparatus and a method for isolation and cytometric analysis of cells from a liquid medium. The contents of WO 2015/118551 are incorporated herein by reference in their entirety.

There is a need for improved methods and systems for performing massive parallel nucleic acid analysis (e.g., transcriptome analysis) of single cells.

SUMMARY OF THE INVENTION

According to one aspect, there is provided a method for parallel analysis of a single cell's nucleic acid, the method comprising:
  (a) receiving a liquid medium containing a suspension of cells to be analyzed into a cell reservoir;
  (b) pumping said liquid medium from an enclosed reservoir, which is separated from said cell reservoir by a cell cage array, until isolated single-cells enter into each cell cage of said cell cage arrays, thereby isolating single-cells in cell cages to produce isolated cells;
  (c) providing a microarray comprising a plurality of DNA spots, wherein each DNA spot comprises a probe and a nucleic acid barcode unique for said DNA spot;
  (d) mounting said cell cage array on said microarray;
  (e) providing said cell cage array with a lysis buffer and a buffer and conditions suitable for nucleic acid synthesis and amplification, thereby producing a library of amplified nucleic acid molecules; and
  (f) sequencing the library of amplified nucleic acid molecules, and determining the cell origin of the sequenced nucleic acid molecules according to the nucleic acid barcode.

According to another aspect, there is provided a system comprising:
  i. a microarray comprising a plurality of DNA spots, each DNA spot comprises a probe comprising a poly-thymine region and a nucleic acid barcode unique for said spot; and
  ii. an apparatus configured to isolate cells from a liquid medium, said apparatus comprises:
    (a) a cell reservoir;
    (b) an enclosed reservoir;
    (c) a cell cage array between said cell reservoir and said enclosed reservoir, each cell cage comprising a large opening adjacent to said first cell reservoir, a cell cage, and at least one small opening adjacent to said enclosed reservoir;
    (d) a liquid medium pump connected to said enclosed reservoir, said pump is configured to move said suspended cells into cell cages by flowing said liquid medium from said cell reservoir through said cell cage array to said enclosed reservoir; and
    (e) a mechanical element which when actuated, pushes said cell cage array against said microarray, thereby said microarray forms a contiguous barrier to said large openings, isolating each cell in each of said cell cages.

This summary is provided to introduce a selection of concepts in a simplified form that are further described below in the detailed description. This summary is not intended to identify key features or essential features of the claimed subject matter, nor is it intended to be used to limit the scope of the claimed subject matter.

DETAILED DESCRIPTION OF THE INVENTION

Definitions

Figure 1:
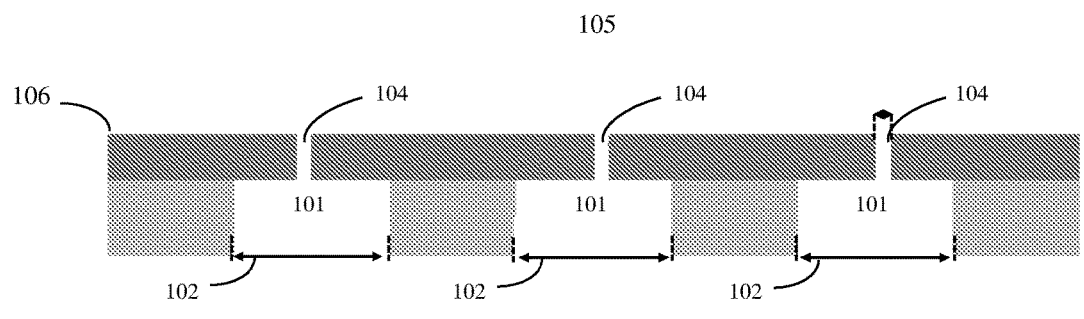
FIGS. 1A-H illustrates, as one embodiment of the present invention, the process for parallel analysis of a single cell RNA expression. (1A). A membrane with micropores is used to capture individual cells in isolated chambers (1B). The membrane with the cells is then mounted onto a DNA microarray with hundreds of thousands of spots of DNA: each spot contains roughly one million DNA molecules all with the same nucleotide sequence (1C). Each spot contains a different variant of that sequence, and acts as a molecular barcode. A gel is added to the membrane (1D) and a solution added to lyse the cells (1E); the gel acting to prevent the leakage of RNAs from the cages. In one embodiment, an RNA-Seq protocol is then carried out on the microarray (reverse transcription (RT), second-strand synthesis (SSS), and in vitro transcription (IVT)) generating free amplified RNA (1F-H).
Figure 1:
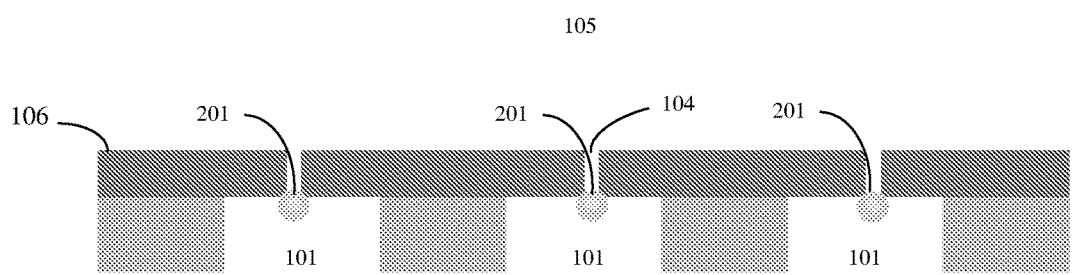
Figure 1:
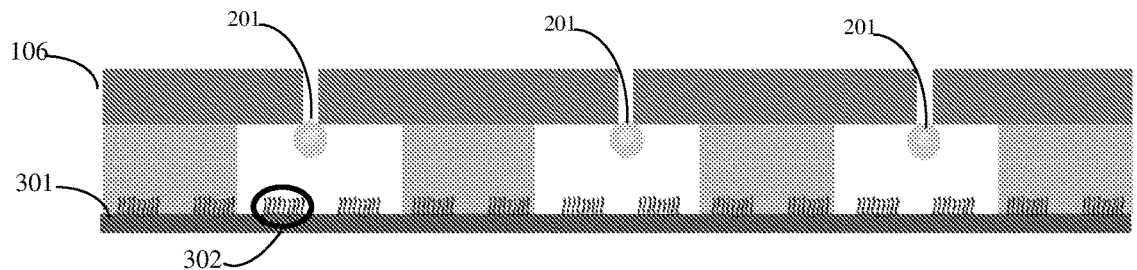
Figure 1:
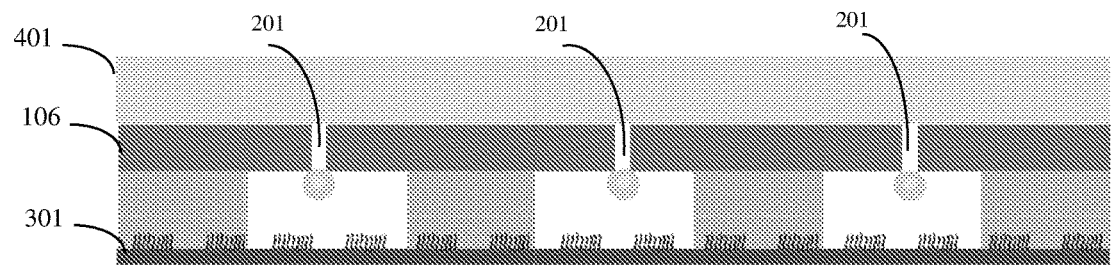
Figure 1:
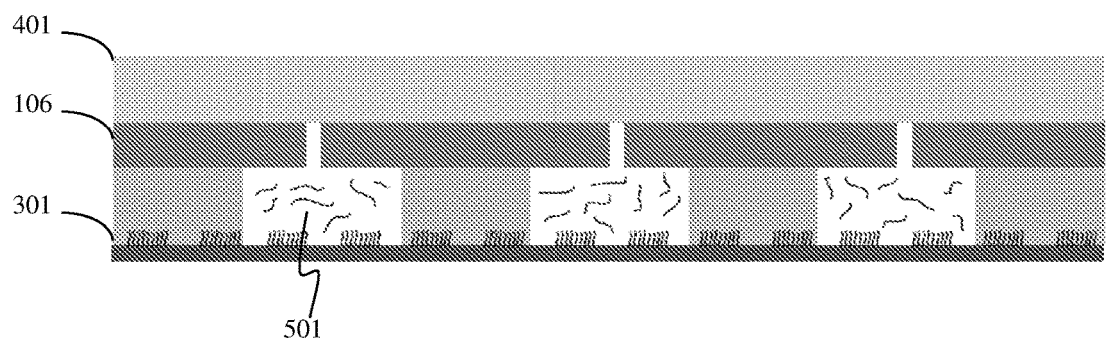
Figure 1:
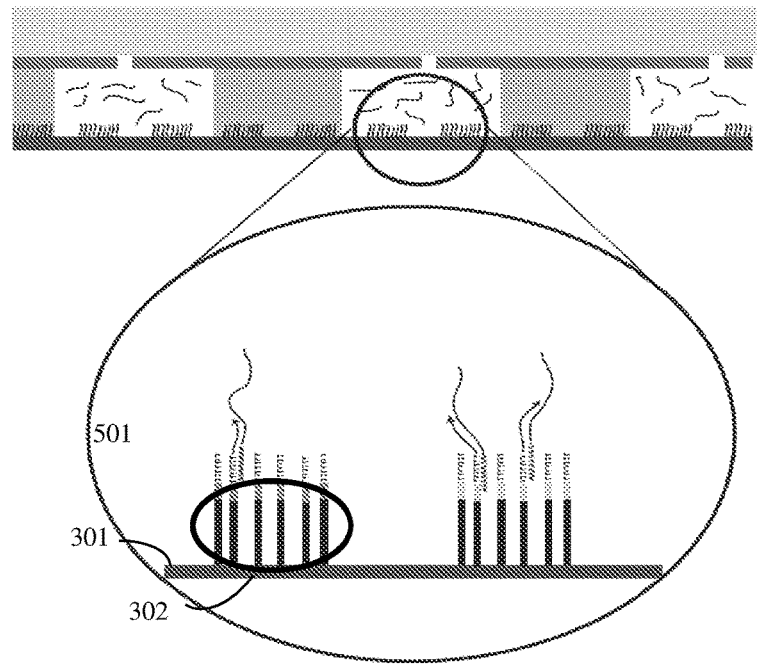
Figure 1:
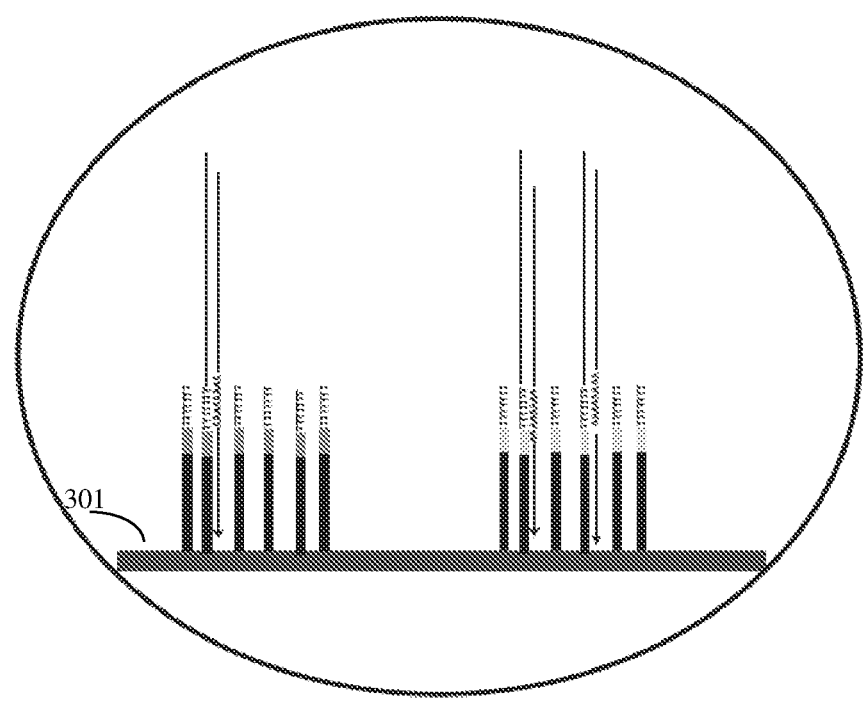
Figure 1:
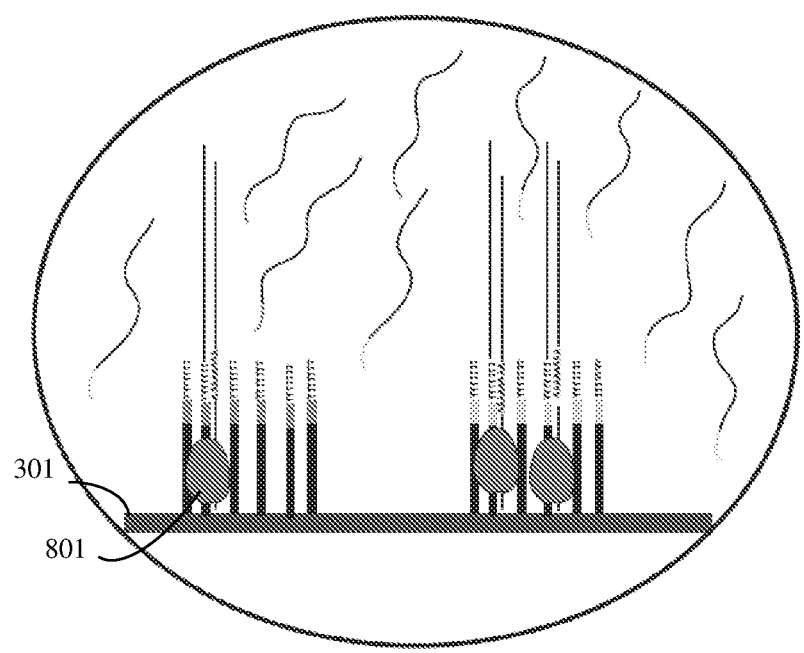

In the discussion unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended. Unless otherwise indicated, the word "or" in the specification and claims is considered to be the inclusive "or" rather than the exclusive or, and indicates at least one of, or any combination of items it conjoins.

In the description and claims of the present application, each of the verbs, "comprise," "include" and "have" and conjugates thereof, are used to indicate that the object or objects of the verb are not necessarily a complete listing of components, elements or parts of the subject or subjects of the verb.

As used herein, a "single cell" refers to one cell. The term "isolated single-cell" refers to a single cell completely, substantially or partially separated, isolated, excluded or purified from other components, e.g., cells, or cell fragments including but not limited to membranes, proteins or nucleic acid molecules.

The term "cell" refers to a functional basic unit of living organisms. Suspended cells from any population can be used in the methods and/or systems described; examples include, but are not limited to, mammalian cells, mammalian mononuclear blood cells, prokaryotic cells, plant cells, eukaryotic single celled organisms including bacteria or yeast, or combinations thereof. Suspended cells can be obtained from tissues in several ways well known in the art. Cells can be easily purified from blood; Mononuclear cells can be released from soft tissues by enzymatic digestion with enzymes such as collagenase, trypsin, or pronase, which break down the extracellular matrix. Alternatively, pieces of tissue can be placed in growth media, and the cells that grow out are available for culture.

As used herein the term "separating", "excluding" or "isolating" is intended to mean that the material has been completely, substantially or partially separated, isolated, excluded or purified from other components, e.g., cells, or cell fragments including but not limited to membranes, proteins or nucleic acid molecules.

In the description that follows, a number of terms related to recombinant DNA technology are used. In order to provide a clear and consistent understanding of the specification and claims, including the scope to be given such terms, the following definitions are provided.

The term "nucleic acid" is well known in the art. A "nucleic acid" as used herein will generally refer to a molecule (i.e., a strand) of DNA, RNA or a derivative or analog thereof, comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C).

The terms "nucleic acid molecule" include but not limited to single-stranded RNA (ssRNA), double-stranded RNA (dsRNA), single-stranded DNA (ssDNA), double-stranded DNA (dsDNA), small RNA such as miRNA, siRNA and other short interfering nucleic acids, snoRNAs, snRNAs, tRNA, piRNA, tnRNA, small rRNA, hnRNA, circulating nucleic acids, fragments of genomic DNA or RNA, degraded nucleic acids, ribozymes, viral RNA or DNA, nucleic acids of infectios origin, amplification products, modified nucleic acids, plasmidical or organellar nucleic acids and artificial nucleic acids such as oligonucleotides.

As used herein, a "transcriptome" refers to the set of all RNA molecules, including mRNA, rRNA, tRNA, and other non-coding RNA transcribed in one cell or a population of cells. "Transcriptome" usually includes the amount or concentration of each RNA molecule in addition to the molecular identities.

As used herein, "RNA-seq" (RNA Sequencing), is a technology that uses the capabilities of next-generation sequencing to reveal a snapshot of RNA presence and quantity from a genome at a given moment in time. CEL-Seq protocol is known in the art as a method for RNA-seq that is used for overcoming the limitation of the small starting amount of RNA, such as described by Hashimshony et al., 2012, *ibid.*, incorporated herein by reference in its entirety. CEL-Seq protocol utilizes barcoding and pooling samples before linearly amplifying mRNA with the use of one round of in vitro transcription. One skilled in the art will appreciate that while the CEL-Seq protocol, as described by Hashimshony et al., 2012, takes place in a suspension, the methods of the nucleic acid synthesis and amplification steps of the present invention make take place in a solid-state, i.e., by use of a microarray. Alternatively, the nucleic acid synthesis and amplification step may take place in suspension by using a photo cleavage linker for binding the oligonucleotide of the DNA spot to a microarray and photo cleaving the oligonucleotide probes.

As used herein, the term "primer" includes an oligonucleotide, either natural or synthetic, that is capable, upon forming a duplex with a polynucleotide template, of acting as a point of initiation of nucleic acid synthesis and being extended from its 3' end along the template so that an extended duplex is formed. Primers within the scope of the present invention bind adjacent to a target sequence. A "primer" may be considered a short polynucleotide, generally with a free 3'—OH group that binds to a target or template potentially present in a sample of interest by either hybridization or ligation, and thereafter promoting polymerization of a polynucleotide complementary to the target.

Primers of the invention, in some embodiments, comprise or consist of nucleotides ranging from 8 to 30 nucleotides. In one aspect, the primer is at least 8 nucleotides, or alternatively at least 9 nucleotides, or alternatively at least 10 nucleotides, or alternatively at least 11 nucleotides, or alternatively at least 12 nucleotides, or alternatively at least 13 nucleotides, or alternatively at least 14 nucleotides, or alternatively at least 15 nucleotides, or alternatively at least 16 nucleotides, or alternatively at least 17 nucleotides, or alternatively at least 18 nucleotides, or alternatively, at least 19 nucleotides, or alternatively, at least 20 nucleotides, or alternatively, at least 21 nucleotides, or alternatively, at least 22 nucleotides, or alternatively, at least 23 nucleotides, or alternatively, at least 24 nucleotides, or alternatively, at least 25 nucleotides, or alternatively, at least 26 nucleotides, or alternatively, at least 27 nucleotides, or alternatively, at least 28 nucleotides, or alternatively, at least 29 nucleotides, or alternatively, at least 30 nucleotides. In one embodiment, the primer is at most 40 nucleotides, or alternatively at most 50 nucleotides, or alternatively at most 75 nucleotides or alternatively at most 100 nucleotides. Primers of the invention, in some embodiments, comprise one or more functional units.

As used herein, a "DNA spot" is a distinct position on a microarray plate at which one or more species of primers/oligonucleotides, also referred to as probes, are immobilized. Typically, these can be a short section of a gene or other nucleic acid element to which a complementary DNA and/or complementary RNA sample can hybridize or ligate, under appropriate conditions, such as high-stringency hybridization conditions. In one embodiment, the probes of each DNA spot are attached, directly or indirectly, to the solid surface of the array.

In some embodiments, the oligonucleotides of each DNA spot is immobilized to the microarray through a photo-cleavable linker. Non-limiting examples of photo-cleavable linkers may include photo-cleavable linkers having an amine group, such as the PC 5'-Amino-Modifier-CE Phosphoramidite, which undergoes photolysis when illuminated with ~360 nm. In embodiments utilizing a photo-cleavable linker, the method of the invention further provides a step of releasing the oligonucleotides of each DNA spot by photo cleavage.

According to an embodiment of the invention, the microarray is a solid surface or substrate. In another embodiment, the solid surface or substrate is a glass chip. In another embodiment, the solid surface or substrate is plastic. In another embodiment, the solid surface or substrate is silicon chip. In another embodiment, the solid surface or substrate is any suitable material known to the person skilled in the art.

The term "hybridization" or "hybridizes" as used herein refers to the formation of a duplex between nucleotide sequences which are sufficiently complementary to form duplexes via Watson-Crick base pairing. Two nucleotide sequences are "complementary" to one another when those molecules share base pair organization homology. "Complementary" nucleotide sequences will combine with specificity to form a stable duplex under appropriate hybridization conditions. For instance, two sequences are complementary when a section of a first sequence can bind to a section of a second sequence in an anti-parallel sense wherein the 3'-end of each sequence binds to the 5'-end of the other sequence and each A, T (U), G and C of one sequence is then aligned with a T (U), A, C and G, respectively, of the other sequence. RNA sequences can also include complementary G=U or U=G base pairs. Thus, two sequences need not have perfect homology to be "complementary" under the invention.

The present invention provides methods and systems for determining the gene expression of all, or a substantial portion of genes at the single cell level for large populations of cells, in parallel. In some embodiments, full or partial transcriptome analysis at single cell level for large populations of cells in parallel, is performed. In some embodiments, targeted transcriptome analysis for one or more genes at single cell level for large populations of cells in parallel, is performed. In other embodiments, full or partial genomic DNA analysis at single cell level for large populations of cells in parallel, is performed.

The present invention shows for the first time massively-parallel nucleic acid analysis of single-cells utilizing a micropore cell capture system and/or method and array-bound DNA primers.

In some aspects of the invention, the methods and/or systems described herein posses the ability to harness DNA microarray technology for the rendering of single-cell RNA-Seq as massively parallel. In one embodiment, the method and/or system described herein allows scaling to millions or more of cells with only simple and inexpensive technology. In another embodiment, the parallel analysis of cells is achieved by the solid-state massively parallel nature of the microarray coupled barcoding. By virtue of the parallel, low volume enzymatic reaction of the method and/or system described herein, low amounts of reagents may be used per cell. In another embodiment, the methods and/or systems described herein lowers the price of gene expression analysis significantly compared to other typical assays known in the art.

According to another embodiment, the present invention provides a method for parallel analysis of single cell's nucleic acid, the method comprises the steps of: receiving a liquid medium containing a suspension of cells to be analyzed into a cell reservoir; pumping the liquid medium from an enclosed reservoir, which is separated from the cell reservoir by a cell cage array, until isolated cells enter into the cell cages, thereby isolating said suspended cells one in each of the cell cages to produce isolated cells; mounting the cell cage array on a microarray comprising a plurality of DNA spots, each DNA spot comprises probes; providing the cell cage with a lysis buffer and a buffer suitable for nucleic acid analysis. In one embodiment, said nucleic acid analysis comprising nucleic acid amplification, thereby providing a library of amplified nucleic acid molecules, wherein the nucleic acid molecules of each cell are determined according to the nucleic acid barcode. In another embodiment, the method comprises sequencing the library of amplified nucleic acid molecules, and determining the cell origin of the sequenced nucleic acid molecules.

According to another embodiment, the present invention provides a method for parallel analysis of a single cell's transcriptome, the method comprises the steps of: receiving a liquid medium containing a suspension of cells to be analyzed into a cell reservoir; pumping the liquid medium from an enclosed reservoir, which is separated from the cell reservoir by a cell cage array, until isolated cells enter into the cell cages, thereby isolating said suspended cells one in each of the cell cages to produce isolated cells; mounting the cell cage array on a microarray comprising a plurality of DNA spots, each DNA spot comprises probes; providing the cell cage with a lysis buffer and a buffer suitable for reverse transcriptase (RT) amplification, thereby providing a library of amplified RNA, wherein the RNA of each cell are determined according to the nucleic acid barcode. In another embodiment, the method further comprises sequencing the library of amplified RNA thereby determining the cell origin of the sequenced RNAs.

According to another embodiment, the step of providing a library of amplified RNA comprises mounting on the cell cage array a gel pad comprising the lysis buffer and/or the buffer suitable for reverse transcriptase (RT) amplification.

According to one embodiment, the step of providing or producing a library of amplified RNA comprises in a subsequent manner: (i) an RT reaction; (ii) a second strand synthesis reaction, and (iii) an amplification reaction, thereby providing a library of amplified RNA. In another embodiment, the second strand synthesis is followed by PCR-based amplification or rolling circle amplification. In another embodiment, the second strand reaction comprises use of a DNA polymerase-1. In another embodiment, said DNA polymerase-1 is an *E. coli* DNA polymerase 1 large Klenow fragment. In another embodiment, said step further comprises a ribonuclease such as a RNase H. In one embodiment, the RNase H generates nicks that serve as primers for DNA polymerase.

The reverse transcription (RT) reaction is well known to one skilled in the art. In one embodiment, the reverse transcription reaction mixture includes a reverse transcriptase, dNTPs and a suitable buffer. In another embodiment, the reaction mixture further comprises other components, such as RNase inhibitor(s). In one embodiment, the desired reverse transcriptase activity may be provided by any suitable enzyme. In another embodiment, the reverse transcriptase enzyme may be selected from the group of: M-MLV, MuLV, A-MLV, HIV, ArrayScript™, Multi-Scribe™, ThermoScript™, PhotoScript® II and SuperScript® I, II, and III enzymes. In one embodiment, the reverse transcriptase reaction may be carried out at any suitable temperature, which will be dependent on the properties of the enzyme. In one embodiment, the reverse transcriptase reaction is performed between 37 to 55° C. In one embodiment, the temperatures outside the range of 37 to 55° C. may also be appropriate. In one embodiment, the reaction time may be as little as 1, 2, 3, 4 or 5 minutes or as much as 48 hours. In another embodiment, the reaction will be carried out between 5 to 120 minutes, or alternatively between 5 to 60 minutes, or alternatively between 5 to 45 minutes, or alternatively between 5 to 30 minutes, or alternatively between 1 to 10 minutes, or alternatively between 1 to 5 minutes, or alternatively any reaction time can be used. According to one embodiment, each dNTP is present in an amount ranging from about 10 to 5000 µM. According to one embodiment, each dNTP is present in an amount ranging from about 20 to 1000 µM. According to one embodiment, the primers and templates for the RT reaction are the probes and the RNA molecules described above.

It will be appreciated to a skilled artisan that an equivalent reaction may be performed to generate a complementary strand of a captured DNA molecule, using an enzyme with DNA polymerase activity. Reactions of this type are well known in the art.

According to one embodiment, the second strand synthesis reaction is performed on the probe bound complementary DNA. In one embodiment, the second strand synthesis is achieved by any suitable means. In another embodiment, the first strand complementary DNA, is incubated with DNA polymerase, dNTPs and a suitable buffer. In another embodiment, a RNA:DNA duplex specific nuclease such as a endonuclease RNase H is used, such as to nick the RNA strand thereby forming primers for the second strand synthesis reaction. In one embodiment, said reaction takes place in a temperature range of 12° C-20° C., 14° C-18° C., or about 16° C.

According to one embodiment, the methods include an amplification step, where the copy number of generated DNA, e.g. complementary DNA molecules is increased. In another embodiment, the amplification may be linear or exponential. In another embodiment, the amplification protocols of interest include, but are not limited to: polymerase chain reaction (PCR) or isothermal amplification or in vitro transcription.

According to one embodiment of the method, the parallel analysis is massively-parallel analysis of up to $10^5$ cells According to one embodiment of the method, the parallel analysis is massively-parallel analysis of up to $10^6$ cells. In another embodiment of the method, the massively-parallel analysis is up to $10^6$ cells. In another embodiment of the method, the massively-parallel analysis is about 10 to $10^6$ cells. In another embodiment of the method, the massively-parallel analysis is about $10^2$ to $10^6$ cells. In another embodiment of the method, the massively-parallel analysis is more than $10^5$ cells.

According to another embodiment of the method, the lysis buffer is a hypotonic buffer containing a detergent. None limiting examples of typical detergents that may be used include Triton X-100, Nonident-P40 or Igepal CA-630 and/or other non-ionic detergents that would not interfere with downstream applications.

According to another aspect, the invention provides a system comprising: a microarray comprising a plurality of DNA spots, each DNA spot comprises a probe and a nucleic acid barcode unique for said DNA spot; and an apparatus configured to isolate cells from a liquid medium, comprising: a cell reservoir; an enclosed reservoir; a cell cage array between said cell reservoir and said enclosed reservoir, each cell cage comprising a large opening adjacent to said first cell reservoir, a cell cage, and at least one small opening adjacent to said enclosed reservoir; a liquid medium pump connected to said enclosed reservoir, said pump is configured to move said suspended cells into cell cages by flowing said liquid medium from said cell reservoir through said cell cage array to said enclosed reservoir; and a mechanical element which when actuated, pushes said cell cage array against said microarray, thereby said microarray forms a contiguous barrier to said large openings, isolating each cell in each of said cell cages.

According to another embodiment of the system, the cell reservoir is configured for receiving a liquid medium containing a suspension of cells.

According to another embodiment of the system, the enclosed reservoir is configured for receiving the liquid medium through the cell cage array from the cell reservoir.

According to another embodiment of the system, each of the cell cages have internal dimensions so that only one cell fits in each cell cage, the large opening has dimensions large enough for the cell to enter the cell cage, and the small openings has dimensions smaller than the cell, prohibiting the cells from exiting the cell cage into the enclosed reservoir. In another embodiment, each of said large opening is, independently between 10 micrometer to 150 micrometer or alternatively about 10 micrometer or alternatively, about 100 micrometer, or alternatively more than 10 micrometer, or alternatively more than 100 micrometer. In another embodiment, each of said small opening is, independently, between 1 micrometer to 8 micrometer, between 1 micrometer to 6 micrometer, between 1 micrometer to 4 micrometer or alternatively about 2 micrometer. In another embodiment, each of said small opening is, independently, less than 10 micrometer, less than 9 micrometer, less than 8 micrometer, less than 7 micrometer, less than 6 micrometer, less than 5 micrometer, less than 4 micrometer, less than 3 micrometer.

According to another embodiment of the system, each of the cell cages has an internal shape of a target cell to be isolated.

According to another embodiment, captured cells block the small openings in their cage, thereby diminishing the force drawing additional cells into that cage, ensuring that no more than a single cell is to be captured in each cage.

According to another embodiment of the system, each of the cell cages has an internal shape selected from the group consisting of a cylindrical shape, an internal conical shape and an internal hemispherical shape.

According to another embodiment, each of said cell cages has internal dimensions large enough to fit single cells of different types. According to another embodiment, each of said cell cages has internal dimensions large enough to fit single cells of different sizes. According to another embodiment, each of said cell cages has internal dimensions large enough to fit single cells of different types and sizes. One skilled in the art will appreciate that cell suspensions analyzed under the method and/or using the system described herein may comprise various populations of cells and/or at various growth stages such as cell cycles. According to another embodiment, each of the cell cages has internal dimensions large enough to fit a single cell.

According to another embodiment of the system, the liquid medium pump is any device from the list of an electrical pump, a micropump, a manual syringe with attached caliper, an automatic programmable syringe, a computerized syringe, a syringe driver, a syringe pump, a programmable syringe pump, a media dispenser, an inductive pump, a pressure injection cell dispenser, a peristaltic pump, and an infusion pump.

According to another embodiment of the system, cell temperature can be manipulated. In another embodiment, the manipulation of the cell temperature is enabled by attaching the system (e.g., the cell cage array or the microarray) to an electrically controlled heat source.

According to another embodiment of the system, between the cell cage array and the enclosed reservoir there is a glass filter support, such that the glass filter support maintains the cell cage array in a flat two dimensional plane.

According to another embodiment of the system, the apparatus is a computerized apparatus comprising at least one user interface, at least one component interface, and at least one processing unit capable of controlling at least one component.

As used herein, a "barcode" refers to a nucleic acid sequence that is used to identify the cell origin of nucleic acid after amplification and sequencing processes. According to the teaching of the present invention, the barcode sequences are unique for each DNA spot. In another embodiment, the unique barcode sequence allows each cell's nucleic acids (genome or transcriptome) to be associated with the original cell. In another embodiment the barcode sequence is used to trace back the genome to each cell. In another embodiment the barcode sequence is used to trace back the transcriptome to each cell. According to one embodiment, the barcode sequence comprises at least 2 nucleotides or alternatively, more than 2 nucleotides, or alternatively, at least 4 nucleotides, or alternatively, at least 6 nucleotides, or alternatively, at least 8 nucleotides, or alternatively, at least 10 nucleotides, or alternatively, at least 12 nucleotides, or alternatively, at least 14 nucleotides, or alternatively, at least 20 nucleotides, or alternatively, at most 8 nucleotides, or alternatively, more than 8 nucleotides, or alternatively, at most 10 nucleotides, or alternatively, at most 14 nucleotides, or alternatively, at most 20 nucleotides.

In some embodiments, the probe of each DNA spot further comprises a Unique Molecular Identifier sequence (UMI). UMI sequences have been described in the art, such as by Kivioja et al., 2012, Nat Methods 9: 72-74. The UMI sequence is a random sequence which may be added to quantify absolute numbers of each transcript molecule and eliminate amplification biases.

According to another embodiment the probe further comprises a nucleotide sequence that is capable of hybridizing to nucleic acids. In another embodiment, the nucleotide sequence that is capable of hybridizing to nucleic acids is located directly or indirectly downstream to the barcode sequence, in the 3' end of the probe. In another embodiment, the nucleotide sequence that is capable of hybridizing to nucleic acids comprises random nucleotide sequence that enables hybridization to RNA. In another embodiment, the nucleotide sequence that is capable of hybridizing to nucleic acids is designed to hybridize to the poly-A tail of mRNA. In another embodiment, the nucleotide sequence, that is capable of hybridizing to the poly-A tail of mRNA, is a poly T sequence. In another embodiment, the nucleotide sequence, that is capable of hybridizing to the poly-A tail of mRNA, is a poly-U oligonucleotide or an oligonucleotide comprised of deoxythymidine analogues. In another embodiment, the poly-T sequence and/or poly-U sequence and/or analogues thereof or a combination thereof comprise at least 6 nucleotides, 7, 8, 9, 10, 11, 12, 13, 14, 15, 16, 17, 18, 19, 20, 30 or 40 nucleotides.

In another embodiment, the probes further comprise a promoter on the 5' end. In another embodiment, the promoter is any promoter that can enables RNA polymerase to transcribe the downstream sequence in the 5' to 3' direction. In another embodiment, the promoter is a T7 promoter. In another embodiment, the probes further comprise an adaptor on the 5' end. In another embodiment, the probes further comprise an adaptor located directly or indirectly downstream to the promoter. In another embodiment, the probes further comprise an adaptor located directly or indirectly upstream to the barcode sequence and/or the hybridizing sequence. In another embodiment, the adaptor is a sequencing adaptor (also known as adapter).

According to an embodiment of the invention, the probes comprise from 5' to 3' a promoter, an adaptor a barcode sequence and a nucleic acids hybridizing sequence. In another embodiment, the probes further comprise a promoter on the 5' end. In another embodiment the different regions of the probe can be directly or indirectly adjacent to each other. In another embodiment, the promoter is a T7 promoter. In another embodiment, the adaptor is a sequencing adaptor. In another embodiment, the nucleic acids hybridizing sequence is a poly-T sequence. In another embodiment there are 4, 5, 6, 7 or 8 random nucleotides directly or indirectly upstream or downstream to the barcode.

According to an embodiment of the invention, the probes are anchored to the surface of the microarray. In another embodiment, the probes are attached to the microarray surface by any suitable means. In another embodiment, the probes are immobilized to the substrate of the array by chemical immobilization. In another embodiment, the probes are immobilized to the substrate of the array directly or indirectly. In another embodiment, the probes are synthesized directly on the substrate.

The present invention provides systems and methods for isolating single cells and performing nucleic acid (e.g., mRNA) analysis to each cell individually. The isolation of the cells is preferably performed using a suction pump to draw the cells from a liquid medium into a perforated cell cage array, where each cage may be of a size so that only one cell may fit. The present invention is based, in part, on the finding that capturing single cells by pumping a cell suspension into a perforated filter as described herein, advantageously enables fast and highly accurate single cell separation. As such, cell capture though pumping results in a single cell inside each of the cell cages since the entering of a single cell into a cell cage results in blockade of the pumping into said cell cage, thereby eliminating the driving force for additional cell to enter the cell cage. Further, as opposed to other cell separation methods (e.g., using gravitation) use of a pumping force can be easily accompanied by simple washing for removal of excess cells or debris.

The perforations of each cell cage may include one large opening, or pore, on the side of the liquid medium with suspended cells to allow one cell to enter each cage, and multiple small openings, or pores, on the side from which the liquid medium is pumped that may be too small for the trapped cell to leave the cage. After the cages are occupied with cells the cage array is mounted on a microarray comprising DNA spots, each DNA spot comprises, in some embodiments, an anchor probe primer and a barcode sequence. In one embodiment, a gel pad comprising a buffer (e.g., buffer suitable for RT amplification) and a lysis buffer (e.g., comprising a detergent) is laid over the membrane. The analysis may be performed by inducing cell lysis and inspecting each cell's contents. The cell cage is where lysis takes place after cells are captured, and is composed of the cell cage array from the top, and the microarray from the bottom. In embodiments wherein transcriptome analysis is requested, the mRNA released from lysed cells known to have a repetitive adenine (Poly-A) tail allowing it to be captured by the Poly-T probe anchored to the array. In some embodiments, the probe further comprises a promoter. In some embodiments, the promoter is a T7 promoter. In some embodiments, the probe further comprises a sequencing adaptor. In some embodiments, the probe comprises from 5' to 3' a T7 promoter, a sequencing adaptor, a unique barcode, and a polyT. Next, the cage array is removed and a second-strand synthesis may be performed, the complementary DNA samples are pooled and consequently comprise sufficient template material for an IVT reaction. The in vitro transcription (IVT) reaction is performed; T7 polymerase binds double stranded DNA on microarray, resulting in amplified RNA. The RNA is fragmented to a size distribution appropriate for sequencing, the 3' adaptor is added by ligation, RNA is reverse transcribed to DNA, and fragments that contain both adaptors and a barcode are selected.

Reference is now made to FIG. 1A-H, which is a schematic illustration of the system and method according to some embodiments of the present invention. The figures illustrate certain embodiments and aspects of the present invention and are not to be construed as limiting the scope thereof. Those skilled in the art will appreciate that many changes could be made in the specific embodiments disclosed herein while still obtaining an identical or similar result. FIG. 1A illustrates a membrane comprising a cell cage array with cylindrical wells for trapping individual cells (106), according to some embodiments of the invention. The cell cage array may contain perforated cell cages (101), each cage has a large opening 102 and a small opening 104. In some embodiments, each of the large opening 102 may be large enough for a single cell to enter each cage on the side adjacent to the cell reservoir 103. In some embodiments, the small openings 104 are small enough to prohibit cells to exit on the side adjacent to the enclosed reservoir 105. In some embodiments, the large and small openings dimensions depend on the size of the target cells. In some embodiments, the large openings can vary from about 10 micrometer to about 150 micrometer. In some embodiments, the small openings can vary from about 1 micrometer to about 8 micrometer. For example, the cell cage array may comprise two polycarbonate membrane filters, bearing 2 micrometer and 10 micrometer holes, respectively. FIG. 1B illustrates a subsequent step of the system and/or method according to an embodiment of the present invention, wherein each cage (101) contains a cell (201) that was isolated from a cell suspension. In some embodiments, the small openings (104) on the side of an enclosed reservoir (105) are connected to a suction pump mechanism; therefore isolation of the cells may be performed using a suction pump to draw the cells from a liquid medium into a perforated cell cage array. FIG. 1C illustrates as one embodiment, a subsequent step wherein the membrane with the cells (106) is then mounted onto a DNA microarray (301) with a plurality (e.g. hundreds of thousands) of spots of DNA (302): each spot may contain roughly one million DNA molecules all with the same nucleotide sequence (probes). Each DNA spot (302) contains a unique variant of that sequence, thereby acting as a molecular barcode. A Poly-T DNA sequence may be used as a probe so as to capture mRNAs known in the art to comprise a Poly-A sequence. FIG. 1D illustrates as an embodiment of a subsequent step addition of (i.e., mounting) a gel (401) on the membrane (106) on the side adjacent to the enclosed reservoir 105. In some embodiments, the gel (401) comprises a lysis solution. In another embodiment, a lyses solution is added to the wells comprising the cells. FIG. 1E illustrates cell lysis and subsequently release of nucleic acid molecules (501) such as RNA. In another embodiment, the gel (401) acts so as to prevent the leakage of nucleic acid molecules from the cages. FIG. 1F shows a subsequent step according to another embodiment of the invention, wherein a single-cell reverse-transcription reaction occurs in each DNA spot, resulting with a complementary DNA bound to the probe. In some embodiments, the anchored probe comprises a polyT sequence for allowing hybridization to the polyA sequence of mRNA and a unique barcode. In some embodiments, the probe acts as the reverse transcription primer and the mRNA is the template. In some embodiments, the primer further comprises a promoter. In some embodiments, the promoter is a T7 promoter. In some embodiments, the primer further comprises a sequencing adaptor. In some embodiments, the adaptor is a 5' Illumina sequencing adaptor. In some embodiments, the primer comprises anchored polyT, a unique barcode, the 5' Illumina adaptor, and a T7 promoter. FIG. 1G illustrates as another subsequent embodiment, performance of a second-strand synthesis after removal of the membrane. Such second strand synthesis may be achieved by suitable means known to a skilled artisan. The complementary DNA samples may be then pooled and consequently comprise sufficient template material for an IVT reaction. FIG. 1H illustrates performance of an in vitro transcription (IVT) reaction as another subsequent step according to an embodiment of the invention. In such embodiment, a polymerase (801), e.g., T7 polymerase, binds double stranded DNA on microarray, resulting in amplified RNA, which can be subsequently harvested.

In exemplary embodiments, RNA libraries are sequenced on the Illumina HiSeq2000 according to standard protocols. In some embodiments that utilize the Illumina HiSeq2000, barcodes has a length of eight nucleotides and designed in groups of four, such that the first five nucleotides will have equal representation of all four nucleotides to allow for template generation and crosstalk corrections that are based on the first four nucleotides read in the Illumina platform. In some embodiments, the barcodes are designed such that each pair is different by at least two nucleotides. According to said embodiment, a single sequencing error will not produce the wrong barcode. A person skilled in the art can recognize that, with minor adjustments of the barcode and primers, libraries can be sequenced using different techniques.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents, and patent applications mentioned in this specification are herein incorporated in their entirety by reference into the specification, to the same extent as when each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The invention claimed is:

1. A method for parallel analysis of nucleic acid of single cells, the method comprising:
   (a) receiving into a cell reservoir a liquid medium containing a suspension of cells to be analyzed;
   (b) pumping said liquid medium from an enclosed reservoir through a cell cage array with a plurality of cell cages, to an enclosed reservoir, thereby isolating single-cells in the cell cages of said cell cage array, wherein the liquid medium flows through large openings, adjacent to said cell reservoir, that are large enough for a single cell to enter each cage on the side adjacent to the cell reservoir, and through small openings, adjacent to said enclosed reservoir, that are small enough to prohibit cells to exit on the side adjacent to the enclosed reservoir;
   (c) associating said cell cage array with a microarray comprising a plurality of DNA spots forming a contiguous barrier to said large openings, to thereby isolate a cell contained in said cell cages, wherein each DNA spot comprises a probe and a nucleic acid identifier sequence unique for said DNA spot, such that each of the DNA spots is exposed to one of the cell cages;
   (d) introducing a buffer and inducing conditions for cell lysis and nucleic acid synthesis and amplification, to produce amplified nucleic acid molecules in the cells; and
   (e) sequencing the amplified nucleic acid molecules, and determining the nature of the amplified and sequenced nucleic acid molecules according to the nucleic acid identifier sequence.

2. The method of claim 1, further comprises removing excess cells or debris between steps (b) and (c).

3. The method of claim 1, wherein step (d) comprises mounting on said cell cage array a gel pad comprising at least one buffer selected from the lysis buffer and the buffer suitable for nucleic acid amplification.

4. The method of claim 1, wherein said conditions comprise: (i) an reverse transcriptase reaction; (ii) a second strand synthesis reaction, and (iii) an amplification reaction to produce amplified RNA.

5. The method of claim 4, wherein said second strand synthesis is selected from, DNA polymerase reaction, PCR-based amplification and rolling circle amplification; and comprises the use of a DNA polymerase 1 and RNase H.

6. The method of claim 1, wherein said probe comprises a promoter.

7. The method of claim 1, wherein said probe comprises a T7promoter.

8. The method of claim 1, wherein the microarray comprises between $10^4$ to $10^6$ cell cages.

9. The method of claim 1, wherein said lysis buffer is a hypotonic buffer containing a detergent.

10. A system comprising:
    i. a microarray comprising a plurality of DNA spots, wherein each DNA spot comprises a probe and a nucleic acid identifier sequence unique for said DNA spot; and
    ii. an apparatus configured to isolate cells from a liquid medium, comprising:
       (a) a cell reservoir configured for receiving a liquid medium containing a suspension of cells;
       (b) a cell cage array, between said cell reservoir and said enclosed reservoir, wherein each cell cage comprises a large opening adjacent to said cell reservoir for receiving cells therefrom the reservoir, and at least one small opening adjacent to said enclosed reservoir;
       (c) a liquid medium pump configured to move said suspended cells into cell cages by flowing said liquid medium from said cell reservoir through said cell cage array to said enclosed reservoir; and
       (d) a mechanical element configured to associate said cell cage array with said microarray, thereby said microarray forms a contiguous barrier to said lame openings, to thereby isolate a cell contained in said cell cages
    wherein said large opening has dimensions sufficient for the cell to enter said cell cage, and said small openings has dimensions smaller than said cell.

11. The system of claim 10, wherein each of said cell cages has an internal shape selected from the group consisting of a cylindrical shape, an internal conical shape and an internal hemispherical shape.

12. The system of claim 10, wherein said liquid medium pump is any device from the list of an electrical pump, a micropump, a manual syringe with attached caliper, an automatic programmable syringe, a computerized syringe, a syringe driver, a syringe pump, a programmable syringe pump, a media dispenser, an inductive pump, a pressure injection cell dispenser, a peristaltic pump, and an infusion pump.

13. The system of claim 10, wherein said apparatus is a computerized apparatus comprising at least one user interface, at least one component interface, and at least one processing unit capable of controlling at least one component.

14. The system of claim 10, wherein the cell cage array comprises between $10^4$ to $10^6$ cell cages.

15. The system of claim 10, wherein each probe of said microarray further comprises a promoter.

16. The system of claim 10, wherein each probe comprises a T7promoter.

17. The system of claim 10, wherein said probe comprises a poly-thymine region.

* * * * *